United States Patent [19]

Willis

[11] Patent Number: 5,074,295
[45] Date of Patent: Dec. 24, 1991

[54] MOUTH-HELD HOLDER

[75] Inventor: James J. Willis, Redding, Calif.

[73] Assignee: Jamie, Inc., Portland, Oreg.

[21] Appl. No.: 388,931

[22] Filed: Aug. 3, 1989

[51] Int. Cl.$^5$ ............................................. A61M 15/00
[52] U.S. Cl. .................. 128/200.24; 128/202.13;
128/201.11; 128/207.11; 362/191
[58] Field of Search .................. 128/200.26, 201.11,
128/206.29, 207.14, 863, DIG. 26, 200.24,
202.13, 207.11; 362/103, 191

[56] References Cited

U.S. PATENT DOCUMENTS

| 2,244,288 | 6/1941 | Colby | 362/191 |
|---|---|---|---|
| 2,299,467 | 10/1942 | Colby | 362/191 |
| 2,521,084 | 9/1950 | Oberto | 128/206.29 |
| 3,418,461 | 12/1968 | Sedlock | 362/191 |
| 4,112,936 | 9/1978 | Blachly | 128/207.14 |
| 4,231,364 | 11/1980 | Speshyock | 128/207.14 |
| 4,270,531 | 6/1981 | Blachly, deceased et al. | 128/207.14 |
| 4,425,911 | 1/1984 | Luomanen et al. | 128/DIG. 26 |
| 4,466,434 | 8/1984 | Brownstein | 128/207.14 |
| 4,495,945 | 1/1985 | Liegner | 128/200.26 |
| 4,664,109 | 5/1987 | Rasocha | 128/207.14 |
| 4,676,240 | 6/1987 | Gardy | 128/207.14 |
| 4,844,061 | 7/1989 | Carroll | 128/DIG. 26 |
| 4,862,903 | 9/1989 | Campbell | 128/206.29 |

Primary Examiner—Edgar S. Burr
Assistant Examiner—Aaron J. Lewis
Attorney, Agent, or Firm—Kolisch, Hartwell, Dickinson, McCormack & Heuser

[57] ABSTRACT

A mouth-held implement holder is disclosed having a socket at one end which receives the butt end of the implement. The opposite end of the holder is formed as a mouthpiece. The mouthpiece, on being inserted into the mouth, is gripped by the molars which extend along the sides of the upper and lower jaws. Provision is made for breathing through the mouthpiece.

7 Claims, 1 Drawing Sheet

MOUTH-HELD HOLDER

BACKGROUND AND SUMMARY OF THE INVENTION

This invention relates to a mouth-held holder, for devices such as tools, instruments, appliances, utensils, etc., broadly referred to herein as implements. The holder enables the user to direct the implement as desired through movement of the jaws and head and without use of the hands.

The holder may be used by persons who do not have use of the arms and hands, to enable such persons to perform work operations with selected tools supported by the holder. The holder also may be and devices to be used by a repairman, mechanic or installer, to enable a such person to effect an end with the hands left free to perform another function. In the case of a person with impaired arm functions, the implement held might be a pen, a brush, or other tool or utensil. In the case of a repairman or mechanic, the implement might be an appliance such as a flashlight. In the specific embodiment of the invention illustrated and described herein, the holder is adapted for the support of a flashlight, although it should be understood that this is for the purpose of illustration only and not intended to limit the invention, as other uses are obviously possible.

Mouth-held holders as known to date commonly are constructed to be gripped by the user through the front teeth and lips. As a consequence, use of the holder over any period of time is tiring and uncomfortable. Furthermore, continued use of the holder creates a risk of injury to the teeth and jaws. Holding on to a device of any size through the lips and front teeth adversely affects the ability of the user to swallow. A common deficiency of implement holders known to date is the lack of any provision enabling breathing through the mouth with the holder in use.

This invention contemplates an implement holder which has a mouthpiece forming one end constructed to be held by biting onto the mouthpiece utilizing the molars extending along the sides of the jaws. The opposite end of the holder may be formed as a socket for seating the end of the implement held by the holder. With the organization contemplated, an implement can be held through the mouth for a considerable period of time without the discomfort experienced through biting with the front teeth. Furthermore, positioning of the implement is possible through relative displacement of the jaw members to produce side-to-side or up-and-down movement without the requirement of tilting the entire head, although implement direction may of course, be changed through head movement. In addition to the above, the invention contemplates, in the organization of a implement holder, a construction whereby breathing through the mouth may be performed while the implement is gripped by the molars.

Accordingly, a general object of the invention is to provide an improved mouth-held implement holder featuring a mouthpiece which enables the holder to be gripped by the molars of the user.

Another object is to provide a mouth-held implement holder which enables a user to breath, if need be, through the mouth when holding the holder.

A related object is to provide such an organization wherein the mouthpiece is bifurcated where such lodges within the mouth, to have laterally spaced molar-gripped portions separated by a tongue-receiving cavity. For comfort reasons, and to provide a construction which is comfortably adaptable to different mouth configurations, the mouthpiece is preferably formed of a flexible and resilient elastomer material.

BRIEF DESCRIPTION OF THE DRAWINGS

These and other objects and advantages are attained by the invention, which is described hereinbelow in conjunction with the accompanying drawings, wherein.

DETAILED DESCRIPTION OF THE PREFERRED EMBODIMENT

Figure 1:
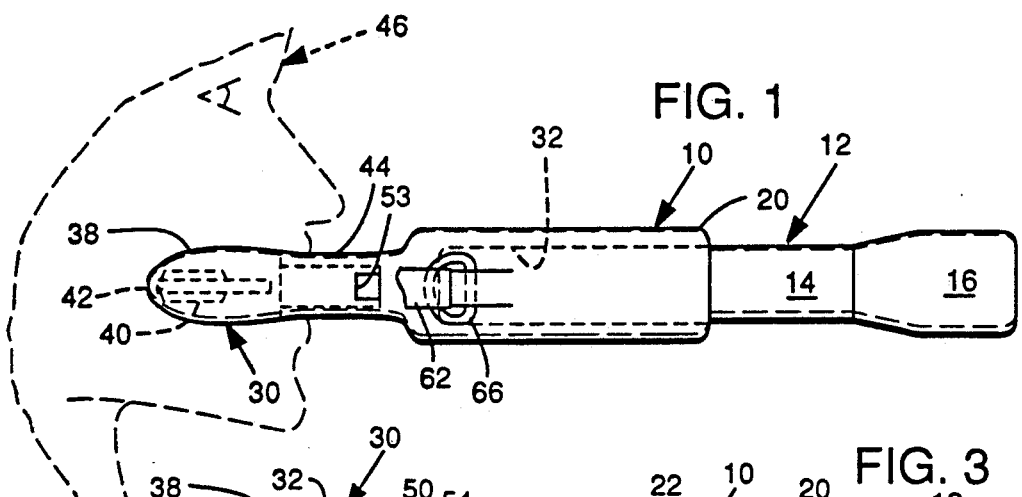
FIG. 1 is a side view of an implement holder, such including a mouthpiece at one end and a socket at its opposite end.
Figure 3:
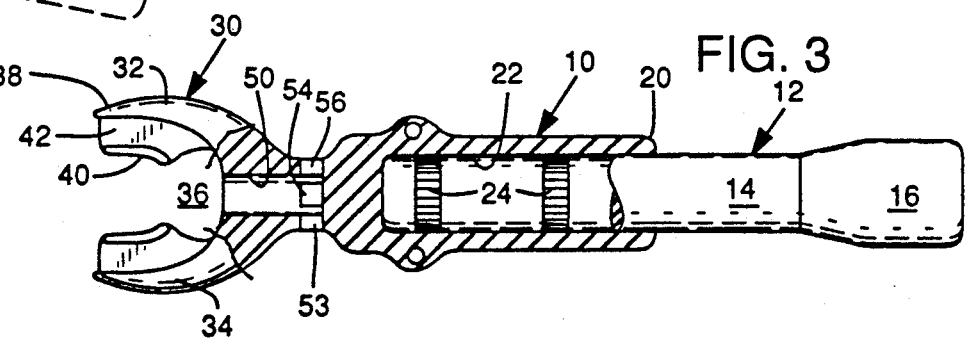
FIG. 3 is a view similar to FIG. 2 but illustrating portions of the holder broken away.

Referring now to the drawings, the holder illustrated, indicated generally at 10, is designed to support a flashlight, although as earlier indicated other holders are possible for supporting other instrumentalities such as a tool, a utensil, a pencil, etc.

The flashlight supported by the holder is indicated generally at 12. Such is conventional and includes an elongate battery housing portion 14 receiving the batteries and an enlarged housing portion 16 housing the usual light reflector and lens. With the flashlight operating, a beam of light extends outwardly and to the right with the holder and flashlight as illustrated in FIG. 1.

Holder 10 takes the form of an elongate body which has formed at one end thereof a socket portion 20. The socket portion has an elongate internal cavity 22 of substantially cylindrical outline which receives the butt end of the flashlight. The inner surface of this cavity may be formed with a ribbing or knurling as shown at 24 to increase the frictional grab of the inside of this cylinder with the external surface of the flashlight housing.

Formed integrally with socket portion 20, and at the left end of the holder, is what is referred to herein as a mouthpiece portion 30. This mouthpiece portion is constructed so as to be fittable within the mouth of a user, and be grippable with biting onto the mouthpiece through the molars which line the sides of the upper and lower jaws of the mouth.

More specifically, the mouthpiece portion is bifurcated and includes a pair of laterally spaced molar-gripped portions indicated at 32 and 34, separated by a tongue-receiving cavity 36. Each molar-gripped portion includes a laterally outer margin as shown at 38 which lodges within the mouth between the outside of the row of teeth and the inside of the cheek. On the inner side of each molar-gripped portion is a flange 40 portion which normally extends along the inside of a row of molars with the mouthpiece held. The molars of the upper and lower jaws engage an expanse 42 which interconnects flange 40 and outer margin 38 earlier described.

Portions 32, 34 have inner ends joined by an expanse of material 44. This expanse is engaged by the lips of the person holding the device and is also referred to herein as a lip-receiving means.

Figure 2:
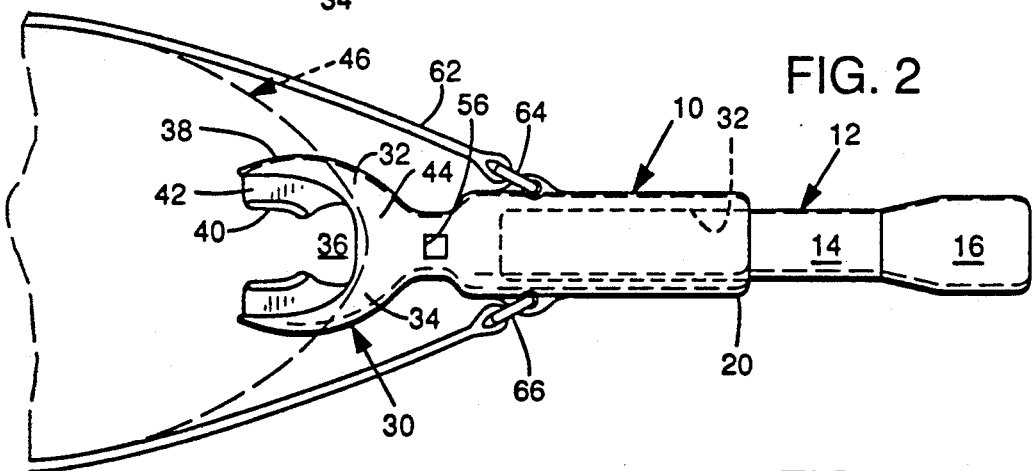
FIG. 2 is a top view illustrating the holder of FIG. 1.
Figure 4:
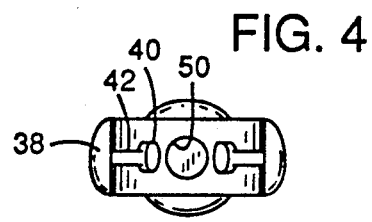
FIG. 4 is a view looking at the end of the holder which includes the mouthpiece.

In FIGS. 1 and 2 portions of the head of a user are outlined in simplified form at 46. The outline indicates how the mouthpiece is fittable within the mouth of the user to be gripped by the molars at the sides of the jaws.

Providing for the breathing of air through the mouth with the mouthpiece portion inserted is an air passage indicated at 50. The air passage has inlets at the top, bottom and sides of the device as indicated at 53, 54, 56, these joining with a common passage that connects with cavity 36.

With the construction illustrated, the user of the device is permitted to breath through the mouth, as well as through the nose. If desired, the user may place the tip of his tongue against port 60 to close off the air passage with breathing then being entirely through the nose.

The body of the holder is preferably made of a flexible and resilient elastomer material. The body as a whole and where such extends between the socket portion and the mouthpiece portion, should have sufficient stiffness so as to result in the socket portion, projecting forwardly from the mouthpiece portion without drooping.

The head can be employed for partially supporting the holder and the flashlight that it mounts. Thus, there is shown a head strap shown at 62 with ends link-connected at 64 and 66 to the flashlight holder between the ends of the holder. The head strap extends from these link connections about the rear of the head.

Whether the head strap is used or not, the holder and the implement that it mounts may be shifted from side-to-side, or up-and-down, through displacing of the lower jaw with respect to the upper jaw, either from side-to-side, or in a back-and-forth manner. This will have the effect of changing the direction in which the implement is printed without tilting or changing the position of the head.

It should be apparent from this description that a device has been illustrated which may be comfortably worn, and which at the same time enables a flashlight or other implement to be positioned without the use of the hands, with such extending directly forwardly and from the mouth. The device is comfortably held with gripping pressure applied by the jaws acting as a whole. Adjustment in position and where the implement is pointed may be produced through displacement of the lower jaw with respect to the upper jaw.

While an embodiment of the invention has been shown and described herein, it is not intended to be limited thereby to specific features of the embodiment disclosed as it should be obvious that variations and modifications are possible without departing from the invention.

It is claimed and desired to secure by Letters Patent:

1. An implement holder adapted to be held by the mouth for holding an end of an implement, the holder comprising:
   a body;
   a socket portion for mounting said end of an implement and the socket portion forming the forward end of said body, said socket portion having an elongate open-ended internal cavity and said end of the implement seating within said cavity,
   a bifurcated mouthpiece including a pair of laterally spaced molar-gripped portions separated by a tongue-receiving cavity forming the rear end of the body, and
   a headband and means mounting said headband on said body disposed forwardly on said body from said mouthpiece, wherein said body includes means defining an air passage extending lengthwise of the holder, and affording, with the mouthpiece gripped by a user, breathing of air through the mouthpiece into the mouth.

2. The holder of claim 1, wherein said molar-gripped portions are composed of an elastomeric material, and wherein said molar-gripped portions are constructed to be gripped by molars in the upper and lower jaws of a user to enable when the jaws are relatively displaced shifting of said body and said socket portion forming one end of said body.

3. The holder of claim 1, wherein the holder has a lip-receiving region engaged by the lips of the user with the holder in use, and wherein said means defining an air passage extends from said cavity to a port disposed forwardly of said lip-receiving region.

4. The combination of an implement and an implement holder:
   the implement having an implement body with forward and rear ends,
   the implement holder having a mouthpiece forming the rear of the holder adapted to be fitted within the mouth of a user and to be gripped by the teeth of the user, the holder having a socket forming the forward end of the implement holder and projecting forwardly of the mouthpiece, the socket having an elongate open-ended internal cavity and the rear end of the implement body seating within said cavity of the socket,
   and means defining an air passage extending through the mouthpiece, with one end of the passage communicating with the interior of the mouth of a user and one of the end of the passage communicating with the atmosphere exteriorally of the mouth.

5. The combination of claim 4, wherein said mouthpiece is bifurcated and includes a pair of laterally spaced molar-gripped portions separated by a tongue-receiving cavity, and wherein said one end of the passage joins with said cavity.

6. The combination of claim 5, wherein said laterally spaced molar-gripped portions are made of an elastomer material, and wherein when said molar-gripped portions are constructed and arranged to be gripped by the molars in the upper and lower jaws of the user, with relative displacement of the jaws producing shifting in the position of the implement.

7. The combination of claim 6, which further includes a head strap adapted to embrace the head of the user, and means disposed forwardly of the mouthpiece mounting the head strap on the implement.

* * * * *